United States Patent
Woehr

(10) Patent No.: US 8,932,257 B2
(45) Date of Patent: Jan. 13, 2015

(54) CATHETER INSERTION DEVICE

(75) Inventor: Kevin Woehr, Melsungen (DE)

(73) Assignee: B. Braun Melsungen AG, Melsungen (DE)

( * ) Notice: Subject to any disclaimer, the term of this patent is extended or adjusted under 35 U.S.C. 154(b) by 3 days.

(21) Appl. No.: 13/498,540

(22) PCT Filed: Oct. 1, 2010

(86) PCT No.: PCT/EP2010/006018
§ 371 (c)(1),
(2), (4) Date: Mar. 27, 2012

(87) PCT Pub. No.: WO2011/038931
PCT Pub. Date: Apr. 7, 2011

(65) Prior Publication Data
US 2012/0184910 A1  Jul. 19, 2012

(30) Foreign Application Priority Data
Oct. 1, 2009 (DE) .................. 20 2009 013 213 U

(51) Int. Cl.
*A61M 5/178* (2006.01)
*A61M 25/06* (2006.01)
*A61M 5/32* (2006.01)

(52) U.S. Cl.
CPC ....... *A61M 25/0606* (2013.01); *A61M 25/0618* (2013.01); *A61M 25/0637* (2013.01); *A61M 2005/325* (2013.01)
USPC ................................ 604/164.07; 604/167.01

(58) Field of Classification Search
CPC ...................... A61M 25/0054; A61M 25/0097

USPC ............. 604/164.07–164.08, 164.12–165.03, 604/523–524, 167.01
See application file for complete search history.

(56) References Cited

U.S. PATENT DOCUMENTS

| 4,673,393 | A | * | 6/1987 | Suzuki et al. ............. 604/167.04 |
| 5,306,253 | A | * | 4/1994 | Brimhall .................. 604/165.03 |
| 5,902,274 | A | * | 5/1999 | Yamamoto et al. ....... 604/164.12 |
| 6,117,108 | A | * | 9/2000 | Woehr et al. .................. 604/110 |
| 2001/0014787 | A1 | * | 8/2001 | Toyokawa et al. ........ 604/167.01 |

FOREIGN PATENT DOCUMENTS

| EP | 1 731 192 A2 | 12/2006 |
| WO | WO 97/21458 A1 | 6/1997 |
| WO | WO 2004/004819 A1 | 1/2004 |
| WO | WO 2006/082607 A1 | 8/2006 |

OTHER PUBLICATIONS

International Search Report completed Nov. 29, 2010 and mailed Dec. 15, 2010 from corresponding International Application No. PCT/EP2010/006018 filed Oct. 1, 2010 (4 pages).
Written Opinion completed Nov. 29, 2010 and mailed Dec. 15, 2010 from corresponding International Application No. PCT/EP2010/006018 filed Oct. 1, 2010 (7 pages).

* cited by examiner

*Primary Examiner* — Nicholas Lucchesi
*Assistant Examiner* — Melissa A Snyder
(74) *Attorney, Agent, or Firm* — Klein, O'Neill & Singh, LLP

(57) ABSTRACT

The present disclosure relates to a catheter insertion device, which comprises a catheter hub in which a check valve is arranged, and a catheter, which is in fluid communication with the catheter hub, wherein a support element is attached to the catheter, and a flexible buffer element is provided between the support element and the catheter hub.

46 Claims, 6 Drawing Sheets

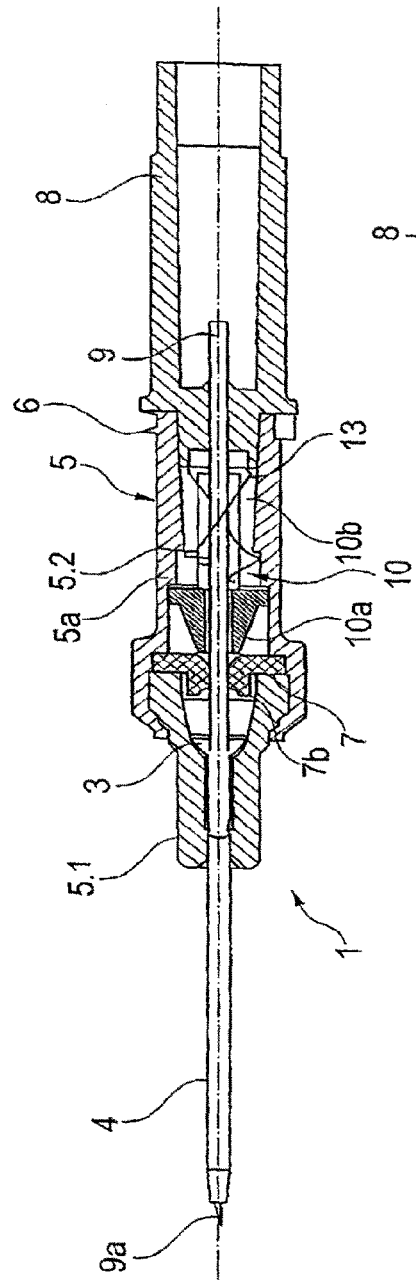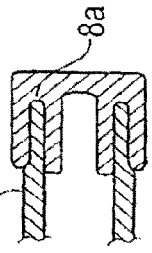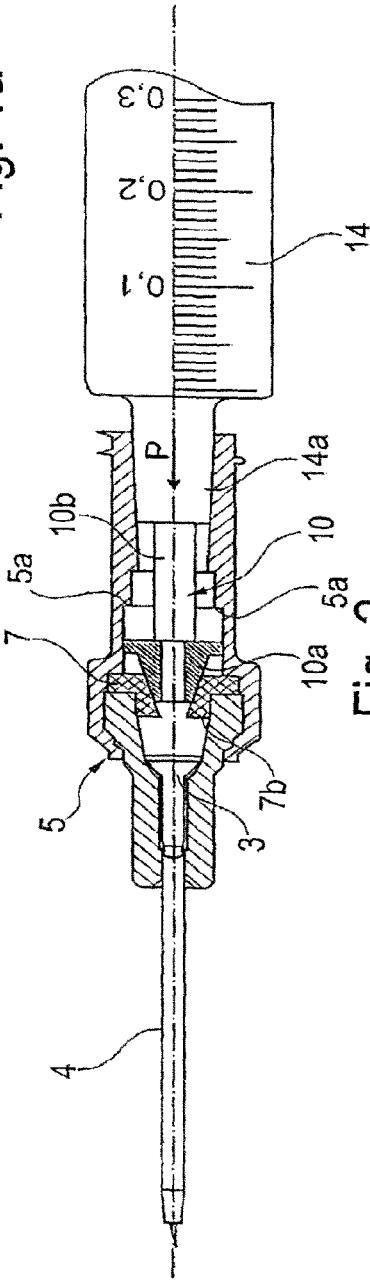
Fig. 1
Prior Art
Fig. 1a
Fig. 2
Prior Art

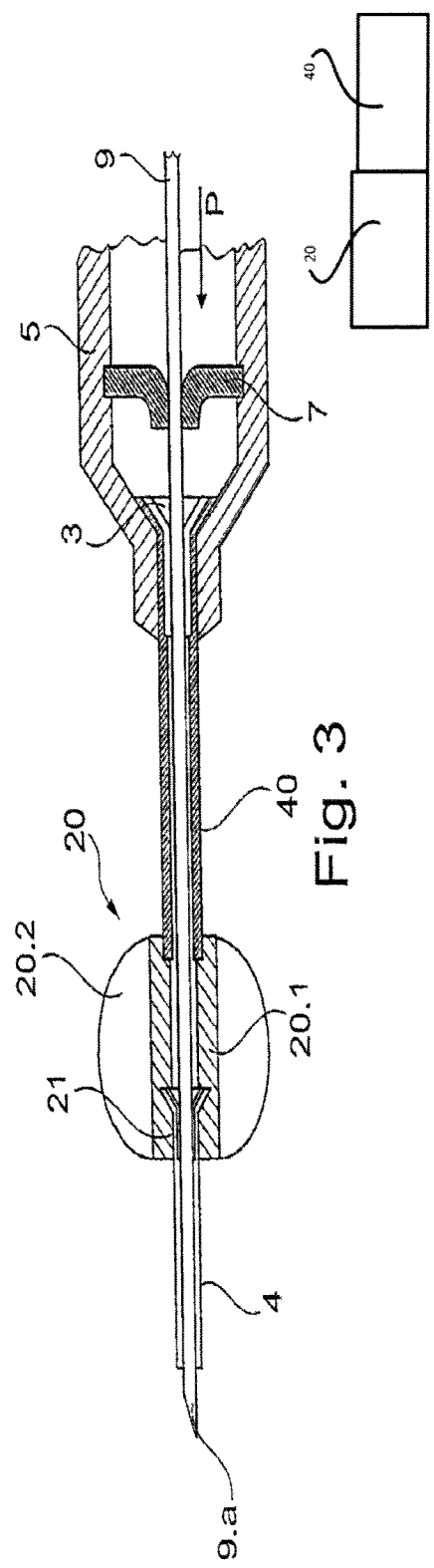
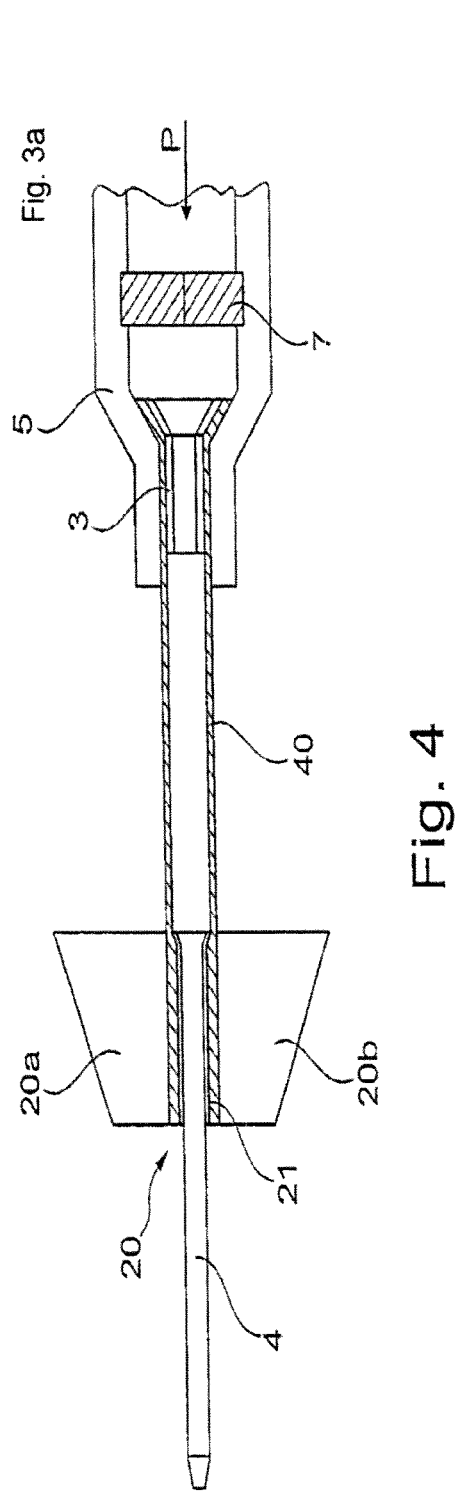

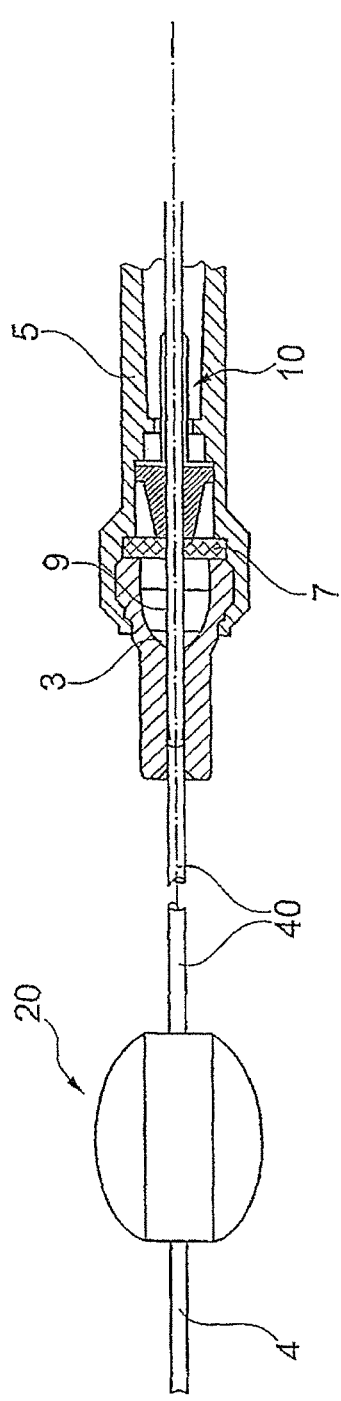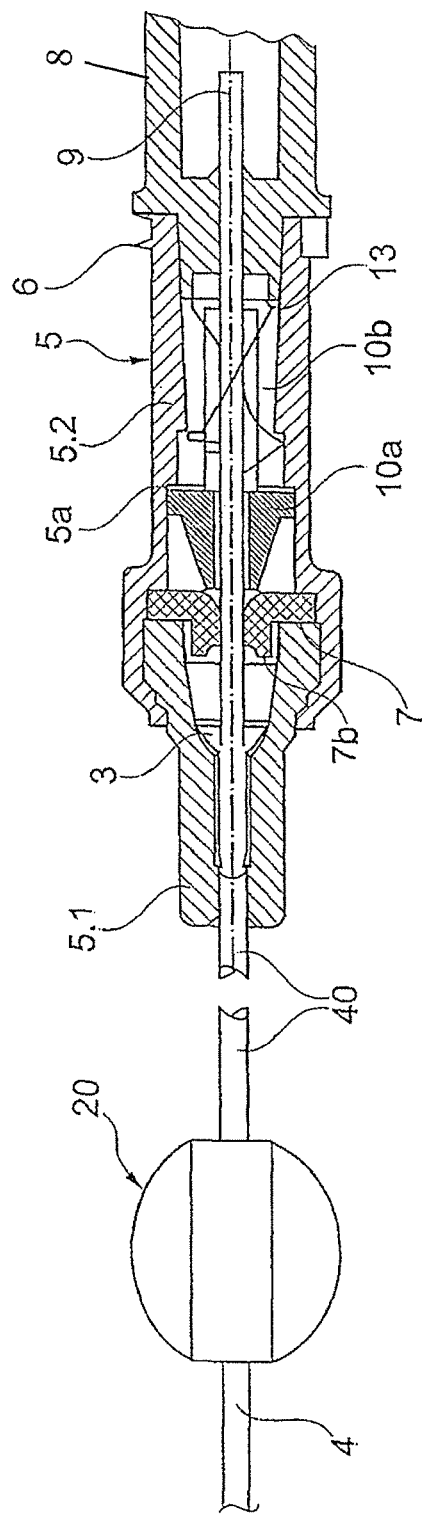

CATHETER INSERTION DEVICE

CROSS-REFERENCE TO RELATED APPLICATIONS

This is a national phase application under 35 U.S.C. §371 of PCT Application No. PCT/EP2010/006018 filed Oct. 1, 2010, which claims the benefit of German application No. 20 2009 013 213 7 filed Oct. 1, 2009, the contents of each of which are expressly incorporated herein by reference.

FIELD OF ART

The present disclosure relates to a catheter insertion device in whose catheter hub a check valve is provided, which prevents the leakage of blood from the catheter hub when the catheter is inserted into the vein of a patient and the needle is removed from the catheter hub.

BACKGROUND

From WO 2004/004819 (FIGS. 1 and 2), such a catheter insertion device is known, having a catheter hub at whose distal end a catheter is attached and in which a check valve is arranged, through which the needle extends in the ready position, wherein the needle tip protrudes distally from the catheter. After retracting the needle out of the catheter hub, the check valve closes automatically, whereupon for example an IV line is attached to the catheter hub so that after opening of the check valve an IV fluid can be introduced into the vein of the patient. Hereby, for example by means of a valve actuation element, the check valve can be opened by pressure in the distal direction. This pressure is transferred to the catheter inserted in the vein of the patient, so that above all in the case of the valve being repeatedly opened and of the related handling of the relatively bulky catheter hub, mechanically induced phlebitis can occur in the patient.

Furthermore, during handling of the catheter insertion device, the problem frequently occurs of the catheter becoming bent. This problem of becoming bent occurs, for example, when the catheter hub is fixed on the skin of the patient, as illustrated by means of FIG. 9. By becoming bent, the catheter becomes unusable and has to be removed, whereupon a new catheter has to be inserted.

SUMMARY

By means of the present disclosure, a catheter insertion device is to be provided, by means of which handling is improved with regard to protection from becoming bent, and mechanically induced phlebitis can be prevented even when, for treating the patient, the valve in the catheter hub has to be repeatedly opened by pressure in the distal direction.

According to the present method, system and device, a support element for the catheter on the skin of the patient is provided between the distal end of the catheter and the catheter hub, and a flexible buffer element is provided between the support element and the catheter hub, especially as an easily deformable, flexible hose line, so that on opening the check valve, forces occurring at the catheter hub are absorbed by the deformation of this flexible hose line and the remaining forces are absorbed by the support element on the skin of the patient, so that no movements are induced at the distal end portion of the catheter positioned in the vein when the check valve in the catheter hub is opened.

Protection from becoming bent is achieved by means of the flexible buffer element or by the flexible hose line between the support element and the catheter hub, in that a possible bend occurs in the area of this flexible hose line, which can be bent straight again, so that no damage occurs to the catheter itself and the uninterrupted passage of the fluid is guaranteed.

Preferably, the flexible and easily deformable hose line is formed between the catheter hub and the support element, independently of the catheter, which extends between the support element and the distal end.

Further aims, advantages, features and application options of the present method, system and device follow from the following description of the embodiments with reference to the drawings. Hereby, all the features described and/or represented by the drawing form the subject matter of the present method, system and device in themselves or in any meaningful combination, independently of their summary in the claims and the back-references thereof.

BRIEF DESCRIPTION OF THE FIGURES

Exemplary embodiments of the present method, system and device are explained in more detail below with reference to the drawings, in which:

FIG. 1 shows a catheter insertion device of the known type,

FIG. 2 shows the insertion of a syringe in the known catheter hub,

FIG. 3 shows in section an embodiment according to the present method, system and device having a support element, and FIG. 3A shows a side view schematic diagram of the interface between the support element and flexible buffer element of FIG. 3.

FIG. 4 shows an embodiment having wings on the support element,

FIG. 5 shows an embodiment having a valve opener in the catheter hub,

FIG. 6 shows an embodiment having a valve opener and a needle guard element,

DETAILED DESCRIPTION

Figure 7:
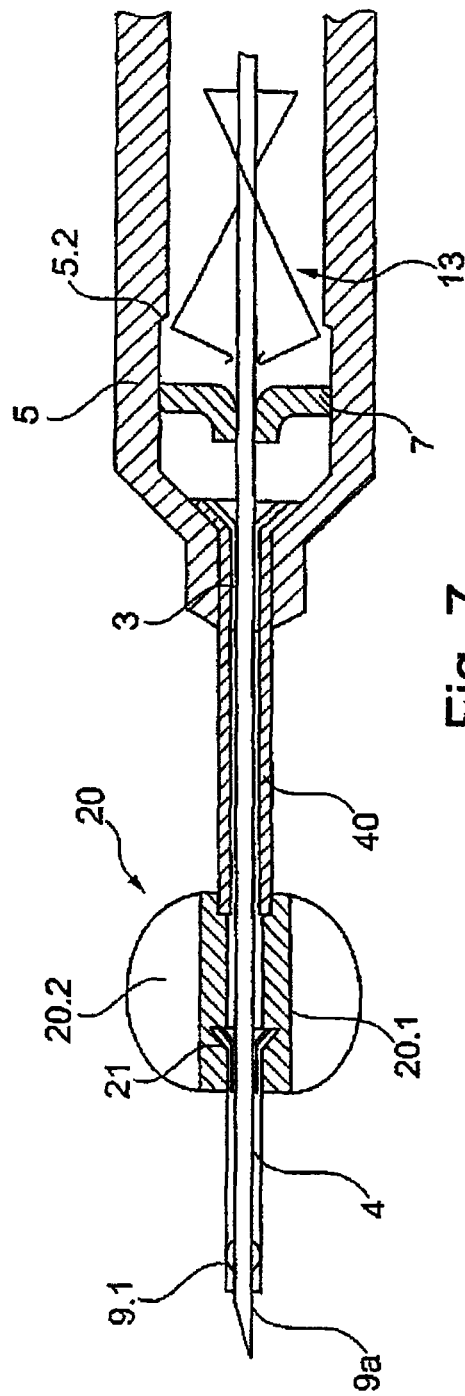
FIG. 7 shows an embodiment having a needle guard element in the catheter hub.

The known catheter insertion device 1 in FIGS. 1 and 2 has a two-part catheter hub 5, wherein between the two elements 5.1 and 5.2 of the catheter hub 5, a disc-shaped check valve 7 is held, which for example has slits starting radially from the middle, through which the needle 9 extends in the ready position (FIG. 1), wherein the needle is held in the needle hub 8. The tip 9a of the needle 9 protrudes over the distal end of the catheter 4 in the ready position. As FIG. 1a shows, a stopper 8a which catches blood is usually provided at the end of the needle hub 8. The stopper which catches blood is provided with a membrane being air-permeable but not blood-permeable. In the catheter hub 5, a valve actuation element 10 is arranged having an approximately truncated cone-shaped front part 10a and two diametrically opposite stays 10b. Between these stays, in the ready position, a needle guard element 13 is located which, by means of the removal of the needle 9 from the catheter hub 5 is removed from the catheter hub 5 and covers the needle tip, after a crimp 9.1 on the needle (shown in FIG. 7) has engaged the proximal rear wall of the needle guard element 13. At 5a, a stop is shown for the valve actuating element 10 which is displaceable in the catheter hub. At 6, a Luer thread is indicated.

FIG. 2 shows the insertion of a syringe 14 in the catheter hub 5, wherein a distal hub 14a displaces the valve actuation element 10 in the catheter hub forwards and opens the valve 7, whose deformed flaps between the slits are designated by 7b. It is obvious that when inserting the syringe 14 in the catheter hub 5, a force P acting in the distal direction is exerted on the catheter hub 5 and thus on the catheter 4, which consists of relatively rigid material. During handling of the catheter hub 5, which is relatively bulky due to the integrated check valve 7, moments of torsion can also be exerted on the catheter 4, by which irritation at the vein is increased.

FIG. 3 schematically shows an embodiment according to the present method, system and device having a support element 20, which has an approximately tubular main body 20.1 with a support area 20.2 for abutting of the support element 20 on the skin of the patient. As shown schematically in FIG. 3A, the support element 20 is formed flat and only slightly higher than the hose line 40. Because the support element 20 is formed very flat, it can hardly be unintentionally jolted, as in the case for the relatively high catheter hub. The catheter 4 is fixed in the support element 20 preferably by means of a metal or plastic hub 21, wherein the catheter consists of a relatively rigid material, usually of fluorinated ethylene propylene (FEP), in other words Teflon. On the proximal side of the support element 20, between the catheter hub 5 and the support element a flexible and easily deformable hose line 40 is provided, which is fixed to the tubular main body 20.1 of the support element 20 by heat-sealing or by means of solvent bonding, if both the support element 20 and the flexible hose line 40 consist of the same soft material. At the catheter hub 5, the flexible hose line 40 can expediently be fixed by means of a metal or plastic hub 3, which has a funnel-shaped hub. The flexible hose line 40 and the support element 20 are preferably manufactured from soft PVC or soft polyurethane. The catheter huh 5 preferably consists of a more rigid polypropylene.

If the flexible hose line 40 and the support element 20 consist of the same soft material, the hose line 40 can also be moulded onto the support element 20. This allows the support element 20 to be formed just as high as the hose line 40.

The flexible, easily deformable hose line 40 forms a buffer element between support element 20 and catheter hub 5 for receiving the forces occurring at the catheter hub 5 during handling, when an IV line is to be attached to the catheter hub 5 or a syringe is to be inserted in the catheter hub. Hereby, both forces in the axial direction can occur at the catheter hub 5, as indicated by an arrow P, and torsional moments can occur, which are absorbed by the buffer element in the form of the flexible hose line 40, so that at the distal end of the catheter 4, no mechanically induced irritations occur in the vein of the patient.

The flexible hose line 40 can also extend only over a certain portion or only partly between the support element 20 and the catheter hub 5.

Figure 9A:
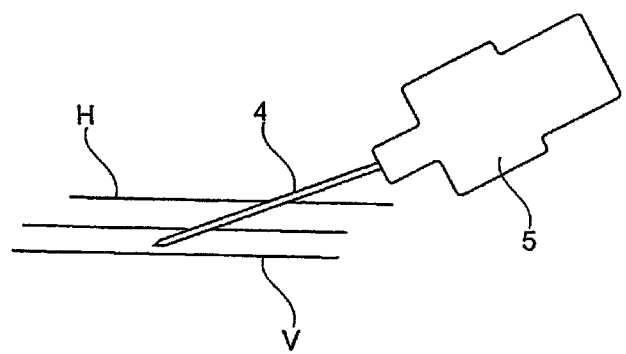
FIG. 9 shows possible bending of the catheter during handling.
Figure 9B:
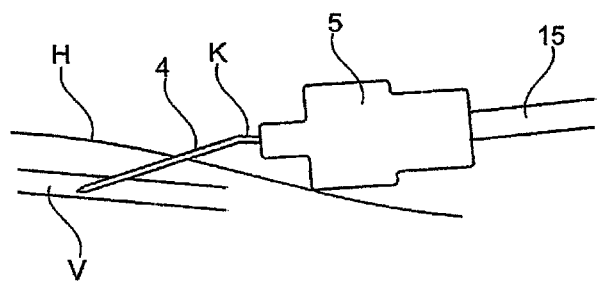

As the catheter 4 is usually formed very thin-walled, the problem frequently occurs in practice that the catheter becomes bent when lateral forces on the catheter hub occur during the handling thereof. In particular, a bend in the catheter can come about when the catheter is first inserted into the skin of the patient at an angle of approximately 30° due to the relatively awkward construction of the catheter hub and then, when the needle is removed from the catheter hub, the catheter comes to bear at an angle of approximately 8° relative to the surface of the skin, wherein the bending of the catheter is favoured by the angle difference occurring thereby. In FIG. 9a, the catheter hub 5 is represented after the insertion of the catheter 4 through the skin H into a vein V and in FIG. 9b an unintentional downwards displacement of the catheter hub 5 is indicated, when, for example, an IV line 15 is attached thereto and/or by incorrect application of adhesive tape for fixing the catheter hub on the skin H the catheter hub is displaced downwards. A bend in the catheter 4 occurring hereby is indicated by K. Such a bend K in the catheter prevents throughflow and is usually irreversible, so that the catheter has to be removed and a new catheter 4 has to be inserted in the vein.

By means of the embodiment according to the present method, system and device having a buffer element between the support element and the catheter hub, protection from bending is additionally provided for the catheter 4, because possible bending between support element 20 and catheter hub 5 occurs at the flexible protective hose line 40 which can be bent straight again after bending, so that throughflow is not impeded. Preferably the flexible hose line 40 is formed thick-walled and manufactured from a correspondingly soft material, so that in the case of bending of the flexible hose line 40, it is not damaged or made unusable.

Thus, by means of the flexible and soft hose line 40, the forces occurring at the catheter hub 5 are to a great extent uncoupled from the support element 20 and especially from the catheter 4.

FIG. 4 schematically shows an embodiment in which a support element 20 is fixedly attached at the relatively rigid distal end portion of the catheter 4, this support element having diametrically opposite wing-like elements 20a and 20b which, during the insertion of the catheter into the vein of the patient, are at first folded together so that the needle 9 can be inserted at a flat angle relative to the surface of the skin, whereupon the two wings 20a and 20b are unfolded and can be fixed on the skin of the patient, for example by means of adhesive tape. After removal of the needle 9 from the catheter insertion device, an IV line or a syringe 14 can be attached at the catheter hub 5, wherein the mechanical pressure P applied for this is absorbed by the flexible hose line 40 as a buffer element.

Various modifications of the described embodiments are possible. For example, the catheter hub 5 can also be formed as one piece and the valve disc 7 can be inserted in a circumferential groove in the catheter hub, as FIGS. 3 and 4 schematically show. Furthermore, a valve actuation element 10 can be omitted, and the syringe hub 14a or an IV line can come to bear directly on the check valve 7 by mechanical pressure P in order to open this valve, as follows from FIG. 3.

FIG. 5 shows an embodiment in which a valve opener or a valve actuation element 10 is arranged in the catheter hub 5.

FIG. 6 shows an embodiment with a valve opener 10 and additionally provided needle guard element 13 in the form of a spring clip having crossed arms. The needle 9 held in the needle hub 8 comprises a tip 9a that protrudes in the ready position over the distal end of the catheter 4. In FIG. 6, the tip 9a and the distal end of the catheter are not shown.

FIG. 7 shows an embodiment in which only a needle guard element 13 is held in the catheter hub 5 in the ready position, without a valve actuation element being provided.

Figure 8:
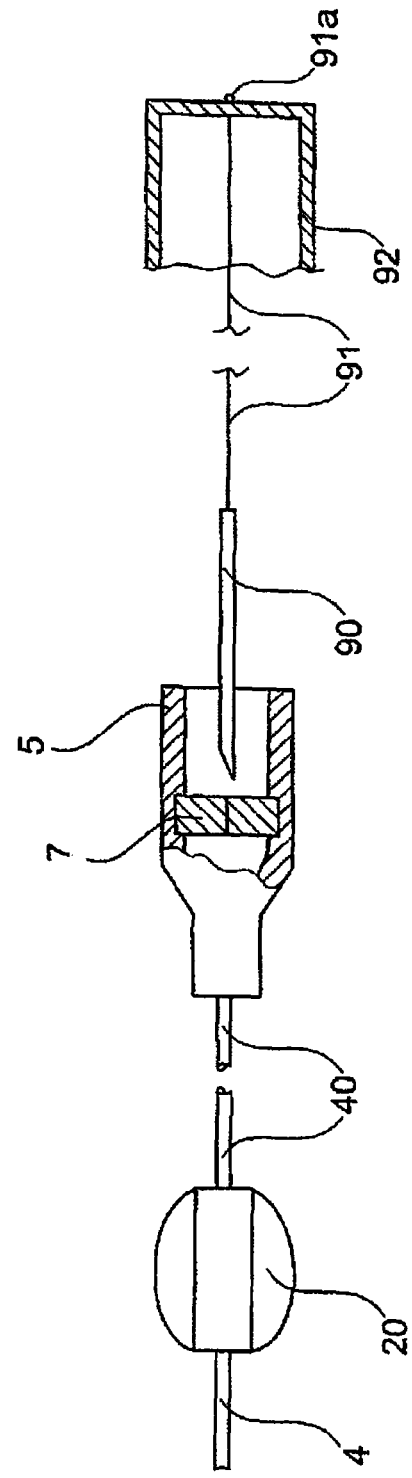
FIG. 8 shows an embodiment in which the needle is provided with an extraction wire.

FIG. 8 shows an embodiment in which a shortened needle 90 is provided in connection with a support element 20, wherein at the proximal end of the shortened needle 90 a wire 91 is fixed, whose proximal end is provided with a bulge 91a which abuts at the proximal outside of a cap 92. In the ready position, the cap 92 is attached to the catheter hub 5, wherein the needle 90 extends through the catheter 4 and the support element 20, and the wire 91 extends through the flexible hose line 40, the valve 7 and the catheter hub 5. After inserting the catheter 4 into the vein of a patient, the cap 92 is detached from the catheter hub 5 and in this way, by means of the wire 91, the needle 90 is withdrawn through the catheter hub 50, whereupon the cap is removed from the catheter hub.

The wire 91 can be connected with the end of the needle 90 by means of welding, bonding or crimping. When one of these types of connection is to close the end of the hollow needle, then a hole must be provided laterally at the proximal end of the hollow needle, to guarantee the passage of blood in the hose line 40. The user recognizes the inflow of blood as a sign that the needle has entered the vein. The blood then flows only up to the valve disc 7.

Alternatively, the wire 91 is connected at the proximal end with a hub 8, as shown in FIG. 1.

The flexible hose line 40 is preferably formed transparent, so that blood flowing up to the valve 7 is clearly visible. Likewise, the tubular body 20.1 of the support element 20 can be formed transparent.

Figure 10:
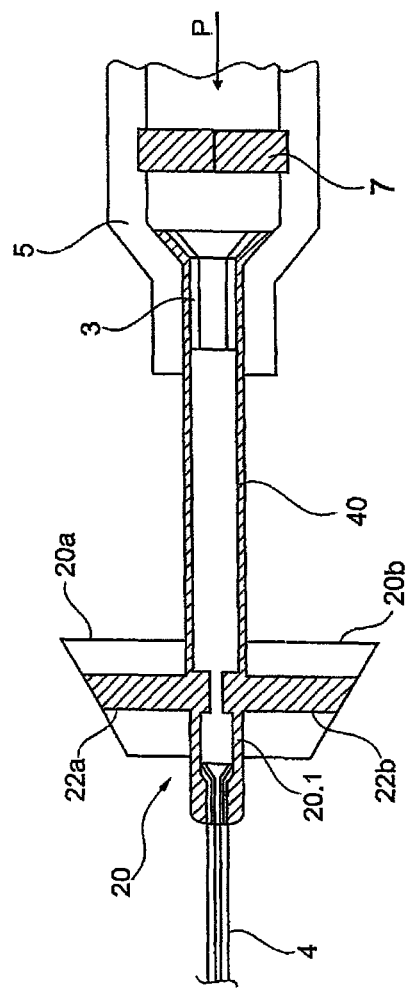
FIG. 10 shows a modified embodiment.

FIG. 10 shows a modified embodiment wherein a releasable clamping means is provided on the support element 20 by means of which the needle 90 can be clamped on the support element when the needle 90 with the catheter 4 is inserted into the vein of a patient. This clamping means is actuated by folding the two wings 20a and 20b together, so that the passage in the support element through which the needle 90 extends is narrowed such that the needle 90 is fixed by clamping. In the embodiment as shown in FIG. 10 a rib 22a and 22b is provided on the two wings 20a and 20b which extend into the tubular main body 20.1 in such a way that the needle 90 can pass between the ribs as long as the wings 20a and 20b extend essentially in the same plain, whereas the needle 90 is clamped between the ends of the ribs 22a and 22b when the two wings 20a and 20b are folded together.

In the embodiment of FIG. 10 a lug is provided on the distal side of the tubular main body 20.1 wherein the catheter 4 is held by means of a metal or plastic hub 21 as it is the case in FIG. 3.

By means of the valve 7 provided in the catheter hub 5, which valve automatically closes after the removal of the needle from the catheter hub and can be reopened as required, especially by a valve opener 10, axial access is guaranteed at the proximal end of the catheter hub 5, through which access a syringe or an IV line can be inserted into the proximal end of the catheter hub 5. This results in a compact and space-saving construction at the catheter hub for an infusion or for blood collection. Hereby, a syringe or an IV line can be inserted in the catheter hub 5 as FIG. 2 shows, or a syringe or an IV line can be connected to the catheter hub 5 via the Luer thread 6 (FIG. 1), to attach a syringe or IV line axially to the catheter hub 5.

The invention claimed is:

1. A catheter insertion device comprising:
a catheter hub in which a check valve is arranged;
a catheter in fluid communication with the catheter hub;
a needle hub having a needle attached thereto and projecting through the catheter hub and the catheter;
wherein a support element is attached to the catheter; and
a flexible buffer element is provided between the support element and the catheter hub and is in fluid communication with both the support element and the catheter hub, the flexible buffer element comprising a thicker wall material than a wall material of the catheter.

2. The catheter insertion device according to claim 1, wherein the flexible buffer element comprises a separate, flexible and easily deformable hose line, the hose line connecting the support element to the catheter hub.

3. The catheter insertion device according to claim 2, wherein the support element and the flexible hose line are manufactured from soft PVC or soft polyurethane.

4. The catheter insertion device according to claim 1, wherein the support element comprises diametrically opposite wings.

5. The catheter insertion device according to claim 1, wherein the check valve comprises radial slits.

6. A catheter insertion device comprising:
a catheter hub in which a check valve having radial slits is arranged;
a catheter in fluid communication with the catheter hub;
a needle hub having a needle attached thereto and projecting through the catheter hub and the catheter;
wherein a support element is attached to the catheter; and
a flexible buffer element is provided between the support element and the catheter hub and is in fluid communication with both the support element and the catheter hub, wherein a needle guard element is provided in the catheter hub.

7. The catheter insertion device according to claim 6, wherein the needle guard element is a spring clip comprising crossing arms.

8. The catheter insertion device according to claim 1, wherein the flexible buffer element comprises a softer material than that of the catheter.

9. A catheter insertion device comprising:
a catheter hub in which a check valve is arranged;
a catheter in fluid communication with the catheter hub;
a needle hub having a needle attached thereto and projecting through the catheter hub and the catheter;
wherein a support element is attached to the catheter; and
a flexible buffer element is provided between the support element and the catheter hub and is in fluid communication with both the support element and the catheter hub, wherein the support element is designed flat with a height dimension in the order of magnitude of a circumference of the flexible buffer element.

10. The catheter insertion device according to claim 9, wherein the support element height dimension equals a circumference of the hose line.

11. The catheter insertion device according to claim 10, wherein the hose line is moulded on the support element or is formed integral to the support element.

12. The catheter insertion device according to claim 1, wherein a hollow needle extends through the catheter hub, the flexible buffer element and the catheter.

13. The catheter insertion device according to claim 1, wherein a hollow needle is connected to a wire, and the hollow needle and the wire extend through the catheter hub, the hose line and the catheter.

14. The catheter insertion device according to claim 13, wherein the support element is provided with wings, the wings being foldable and extending on opposite sides of a tubular main body, wherein when the wings are folded, a releaseable clamping means is provided for clamping the needle in the tubular main body.

15. A catheter insertion device comprising:
a catheter hub in which a check valve is arranged;
a catheter in fluid communication with the catheter hub;
a needle hub having a needle attached thereto and projecting through the catheter hub and the catheter;
wherein a support element is attached to the catheter; and
a flexible buffer element is provided between the support element and the catheter hub and is in fluid communication with both the support element and the catheter hub, wherein the flexible buffer element comprises a transparent material.

16. A catheter insertion device comprising:
a catheter hub comprising a body defining an interior cavity in which a check valve and a valve actuator are arranged;
a catheter in fluid communication with the catheter hub;
a support element attached to the catheter and to a flexible buffer element, which is provided between the support element and the catheter hub and is in fluid communication with both the support element and the catheter hub;
a hollow needle extending through the catheter hub, the flexible buffer element and the catheter; and
wherein the check valve is actuated by the valve actuator when a syringe is inserted into a proximal opening of the catheter hub.

17. The catheter insertion device according to claim 16, wherein the support element comprises diametrically opposite wings.

18. The catheter insertion device according to claim 16, wherein the check valve comprises radial slits.

19. The catheter insertion device according to claim 16, wherein the flexible buffer element comprises a thicker wall material than a wall material of the catheter.

20. The catheter insertion device according to claim 16, wherein a needle guard element is positioned in the catheter hub.

21. The catheter insertion device according to claim 20, wherein the needle guard element is a spring clip with crossing arms.

22. The catheter insertion device according to claim 16, wherein the hollow needle is connected to a wire and the hollow needle and the wire extend through the catheter hub, the hose line and the catheter.

23. A method for manufacturing a catheter insertion device comprising:
forming a catheter hub comprising a body defining an interior cavity and placing a check valve therein;
connecting a support element at a distal end to a catheter and at a proximal end to a flexible buffer element and connecting the flexible buffer element to the catheter hub, the catheter being in fluid communication with the catheter hub, and the flexible buffer element comprises a thicker wall material than a wall material of the catheter;
extending a hollow needle through the catheter hub, the flexible buffer element and the catheter;
positioning a needle guard in the catheter hub and proximal of the check valve; and
wherein the support element and the buffer element are located between the catheter and the catheter hub.

24. The method according to claim 23, wherein the support element comprises diametrically opposite wings.

25. The method according to claim 23, wherein the check valve comprises radial slits.

26. The method according to claim 23, wherein a needle guard element is a spring clip.

27. The method according to claim 26, wherein the spring clip has crossing arms.

28. The method according to claim 23, further comprising an actuator configured for opening the check valve.

29. The method according to claim 28, further comprising the step of removing the needle from the catheter hub, the flexible buffer element and the catheter.

30. The method according to claim 29, further comprising placing a syringe tip or an IV line into a proximal end of the catheter hub and advancing the actuator distally.

31. The catheter insertion device according to claim 6, wherein the flexible buffer element comprises a separate, flexible and easily deformable hose line, the hose line connecting the support element to the catheter hub.

32. The catheter insertion device according to claim 7, wherein the support element and the flexible hose line are manufactured from soft PVC or soft polyurethane.

33. The catheter insertion device according to claim 6, wherein the support element comprises diametrically opposite wings.

34. The catheter insertion device according to claim 6, wherein the check valve comprises radial slits.

35. The catheter insertion device according to claim 6, wherein the flexible buffer element comprises a softer material than that of the catheter.

36. The catheter insertion device according to claim 6, wherein a hollow needle extends through the catheter hub, the flexible buffer element and the catheter.

37. The catheter insertion device according to claim 6, wherein a hollow needle is connected to a wire, and the hollow needle and the wire extend through the catheter hub, the hose line and the catheter.

38. The catheter insertion device according to claim 37, wherein the support element is provided with wings, the wings being foldable and extending on opposite sides of a tubular main body, wherein when the wings are folded, a releaseable clamping means is provided for clamping the needle in the tubular main body.

39. The catheter insertion device according to claim 9, wherein the flexible buffer element comprises a separate, flexible and easily deformable hose line, the hose line connecting the support element to the catheter hub.

40. The catheter insertion device according to claim 39, wherein the support element and the flexible hose line are manufactured from soft PVC or soft polyurethane.

41. The catheter insertion device according to claim 1, wherein the support element comprises diametrically opposite wings.

42. The catheter insertion device according to claim 9, wherein the check valve comprises radial slits.

43. The catheter insertion device according to claim 9, wherein the flexible buffer element comprises a softer material than that of the catheter.

44. The catheter insertion device according to claim 9, wherein a hollow needle extends through the catheter hub, the flexible buffer element and the catheter.

45. The catheter insertion device according to claim 9, wherein a hollow needle is connected to a wire, and the hollow needle and the wire extend through the catheter hub, the hose line and the catheter.

46. The catheter insertion device according to claim 45, wherein the support element is provided with wings, the wings being foldable and extending on opposite sides of a tubular main body, wherein when the wings are folded, a releasable clamping means is provided for clamping the needle in the tubular main body.

* * * * *

UNITED STATES PATENT AND TRADEMARK OFFICE
CERTIFICATE OF CORRECTION

| | | |
|---|---|---|
| PATENT NO. | : 8,932,257 B2 | Page 1 of 1 |
| APPLICATION NO. | : 13/498540 | |
| DATED | : January 13, 2015 | |
| INVENTOR(S) | : Kevin Woehr | |

It is certified that error appears in the above-identified patent and that said Letters Patent is hereby corrected as shown below:

In the Specification

In column 1, line 8-9, delete "20 2009 013 213 7" and insert -- 20 2009 013 213.7 --, therefor.

In column 2, line 31, delete "FIG. 3." and insert -- FIG. 3, --, therefor.

In column 3, line 37, delete "huh" and insert -- hub --, therefor.

In the Claims

In column 6, line 58, in claim 14, delete "releaseable" and insert -- releasable --, therefor.

In column 8, line 32, in claim 38, delete "releaseable" and insert -- releasable --, therefor.

Signed and Sealed this
Twenty-first Day of July, 2015

Michelle K. Lee
*Director of the United States Patent and Trademark Office*